(12) United States Patent
Radomski et al.

(10) Patent No.: US 8,490,621 B2
(45) Date of Patent: Jul. 23, 2013

(54) DEVICE FOR RESPIRATING PATIENTS

(75) Inventors: Klaus Radomski, Lübeck (DE); Jochim Koch, Ratzeburg (DE)

(73) Assignee: Dräger Medical GmbH, Lübeck (DE)

( * ) Notice: Subject to any disclaimer, the term of this patent is extended or adjusted under 35 U.S.C. 154(b) by 1116 days.

(21) Appl. No.: 12/395,856

(22) Filed: Mar. 2, 2009

(65) Prior Publication Data

US 2009/0250055 A1    Oct. 8, 2009

(30) Foreign Application Priority Data

Apr. 7, 2008 (DE) .......................... 10 2008 001 022

(51) Int. Cl.
*A61M 16/01* (2006.01)
*A61M 16/16* (2006.01)

(52) U.S. Cl.
USPC ................................ 128/203.13; 128/203.16

(58) Field of Classification Search
USPC ........................... 128/200.24, 203.14–203.16
See application file for complete search history.

(56) References Cited

U.S. PATENT DOCUMENTS

| 4,629,333 | A | * | 12/1986 | Dosoretz et al. | 374/20 |
| 5,468,961 | A | * | 11/1995 | Gradon et al. | 250/343 |
| 6,039,696 | A | * | 3/2000 | Bell | 600/532 |

FOREIGN PATENT DOCUMENTS

DE    20 2007 004 24    6/2007

* cited by examiner

*Primary Examiner* — Stephen Crow
(74) *Attorney, Agent, or Firm* — McGlew and Tuttle, P.C.

(57) ABSTRACT

A device is provided for increasing humidity for respirating patients, especially for a respiration humidifier or an anesthesia reflector. The device includes a gas channel for passing through breathing air, a control and/or regulating device, a temperature sensor and a dew sensor for measuring the humidity present in the breathing air by electromagnetic radiation with a generating device and with a detection device for electromagnetic radiation. The humidity of the breathing air is determined at a low cost and in a reliable manner and condensation is avoided in the respiration system without any additional effort for sterilization. Humidity in the breathing air is determined by the a dew sensor by the change in the reflection of the electromagnetic radiation as a function of dew formation at a condensation-fogged and condensation-free boundary surface between breathing air and a medium having an optical density higher than that of breathing air.

19 Claims, 4 Drawing Sheets

DEVICE FOR RESPIRATING PATIENTS

CROSS REFERENCE TO RELATED APPLICATIONS

This application claims the benefit of priority under 35 U.S.C. §119 of German Patent Application DE 10 2008 001 022.7 filed Apr. 7, 2008, the entire contents of which are incorporated herein by reference.

FIELD OF THE INVENTION

The present invention pertains to a device for respirating (also known as ventilating) patients, especially a respiration humidifier or anesthesia reflector. The present invention pertains, furthermore, to a process for controlling and/or regulating the humidity of breathing air in a device for respirating patients.

BACKGROUND OF THE INVENTION

Respiration humidifiers are necessary during the artificial respiration of patients, in whom the function of the nose is bridged over by a tube. The inspired air must therefore be humidified and optionally heated to physiological values during artificial respiration to preserve the lung function.

Inhalative sedation or anesthesia of patients is necessary for various medical applications, e.g., during surgery. Anesthesia reflectors are used to transfer the anesthetic from the expiration gas breathed out by the patient to the inspiration gas to be breathed in by the patient (reflection) and thus to make multiple utilization possible and not to increase the concentration of anesthetic in the room in which the patient is located. Furthermore, the anesthesia reflector shall humidify and optionally heat the inspired air to physiological values.

Humidity sensors are used in respiration humidifiers and anesthesia reflectors in order to determine the humidity in the breathing air, i.e., the inspired gas and/or the expired gas. The data measured by the humidity sensors are used to control and regulate the humidity of the breathing air.

The use of humidity sensors with inexpensive measurement methods, e.g., a capacitive humidity measurement, is too inaccurate. The use of the dew point-mirror principle of measurement is too expensive for application in respiration humidifiers. Such sensors are, moreover, arranged in the breathing air, i.e., in a gas channel or a humidifying chamber, so that there are bacteriological problems.

U.S. Pat. No. 5,468,961 shows a humidity sensor for a device for respirating patients. Breathing air, whose humidity is to be determined, is sent through a sample cell. An infrared light source generates infrared light, which is sent through the sample cell and is subsequently detected by a detector. The humidity contained in the breathing air absorbs the infrared light, so that the quantity of infrared light detected by the detector decreases with increasing humidity in the breathing air and vice versa. The manufacture of the infrared light source, detector as well as sample cell is expensive. Furthermore, complicated means are needed to avoid the condensation of water on the inner surface of the sample cell.

SUMMARY OF THE INVENTION

The object of the present invention is therefore to make available a device for respirating (ventilating) patients and a process for controlling and/or regulating the humidity of breathing air in a device for respirating patients, in which the humidity of the breathing air can be determined at a low cost and in a reliable manner. Furthermore, the device for respirating patients shall not cause any additional effort for sterilization.

This object is accomplished with a device for respirating patients, especially with a respiration humidifier or with an anesthesia reflector, comprising means for increasing the humidity and/or the anesthetic concentration in breathing air, at least one gas channel for passing through breathing air, a control and/or regulating means, at least one temperature sensor and at least one dew sensor for measuring the humidity contained in the breathing air with a generating means and with a detection means for electromagnetic radiation, wherein the at least one dew sensor determines a change in the reflection of the electromagnetic radiation at a boundary surface between breathing air and a medium having an optical density higher than that of air as an indicator of a change in dew formation at said boundary surface.

The degree of reflection of the electromagnetic radiation is affected as a function of dew formation. The boundary surface may be fogged with water of condensation or free from water of condensation.

In another embodiment, the denser medium is a solid. Solids can be easily installed in tubes and housings. In addition, humidity can lead to water vapor readily condensing on solids.

In an additional embodiment, the denser medium is glass or a plastic transparent to electromagnetic radiation, e.g., Plexiglas. The electromagnetic radiation can thus be introduced into the medium having a higher optical density on a first side. The boundary surface, on which humidity can be deposited, is located on a second side of the medium having a higher optical density. The first and second sides are preferably located opposite each other. The medium having the higher density can thus be easily installed in tubes and/or housings. Furthermore, a transmitting and receiving diode can be detachably fastened to the medium having the higher density, e.g., glass or Plexiglas, on the first side.

The electromagnetic radiation is preferably light.

In another embodiment, the boundary surface is arranged at the means for increasing the concentration of humidity and/or anesthetic in the breathing air.

In another variant, the boundary surface is an inner side of the at least one gas channel for passing through breathing air.

The solid is advantageously heatable by means of a heater preferably integrated in the solid. The water condensed on the solid because of a high humidity in the breathing air causes the electromagnetic radiation to be always reflected only partially at the boundary surface and to also be refracted, so that the dew sensor always measures a high humidity, even though the humidity in the breathing air may already have dropped again. The water of condensation is briefly evaporated with the heater. The solid preferably has a low mass, so that the solid cools rapidly after heating, and, in particular, the breathing air contributes to rapid cooling of the solid. The electromagnetic radiation is again reflected totally and is not refracted at the boundary surface after evaporation of the water of condensation on the solid and after cooling of the solid. High humidity can again be measured in the breathing air because condensation of water on the solid brings about a change in the degree of reflection of the electromagnetic radiation.

Additional sensors for other parameters, e.g., temperature, $CO_2$ or breathing gas volume, are arranged at the at least one dew sensor in an additional embodiment.

The additional sensors and the at least one dew sensor are preferably integrated in a sensor block. As a result, the sensors can be attached in a compact form, e.g., to a tube or housing.

In another embodiment, the solid of the medium having the higher density is designed as a sample holder and/or a wall of at least one gas channel or of a housing of the means for increasing the humidity and/or the anesthetic concentration in breathing air. The solid thus forms part of the wall of the gas channel or of the housing, so that no additional body has to be arranged in the area through which the breathing air flows.

A process according to the present invention for controlling and/or regulating the humidity of breathing air in a device for respirating patients has the following steps: Measurement of the humidity contained in the breathing air by means of at least one dew sensor, analysis of the data determined by the at least one dew sensor and control and/or regulation of the humidity in the breathing air on the basis of the data measured by the at least one dew sensor, wherein the detection of the humidity in the breathing air is carried out with the steps of generating an electromagnetic radiation, especially light; sending the electromagnetic radiation to a boundary surface between breathing air and a medium having an optical density higher than that of breathing air; at least partial reflection of the electromagnetic radiation at the boundary surface; detection of the electromagnetic radiation reflected at the boundary surface only; and analysis of the quantity of reflected electromagnetic radiation to determine the humidity in the breathing air.

In another embodiment, the medium having a higher density is a solid, especially glass or a plastic more transparent to electromagnetic radiation, e.g., Plexiglas.

In another variant, the humidity is increased in the breathing air until the humidity reaches a limit value. The limit value is, in general, a relative humidity of 100% or nearly 100%. The breathing air as an inspiration gas is said to have normally a relative humidity of about 100%.

In particular, the humidity in the breathing air is increased until a reduction in the reflection of the electromagnetic radiation occurs because of the formation of water of condensation on the surface of the solid.

In an additional embodiment, the solid is heated during the formation of water of condensation on the surface of the solid in order to evaporate the water of condensation.

The humidity in the breathing air is preferably reduced when a limit value of the humidity in the breathing air is reached.

In another variant, the humidity in the breathing air is reduced when the reflection of the electromagnetic radiation decreases because of the formation of water of condensation on the surface of the solid. A reduction in humidity is normally necessary when water of condensation forms on the medium having a higher density, especially glass or Plexiglas. The raising or lowering of the humidity makes it possible to regulate the humidity in the breathing air in the range of 100% relative humidity.

The raising or reduction of humidity in the breathing air is advantageously achieved by increasing or reducing the temperature in a humidifying chamber of a respiration humidifier or the heating power supplied.

Six exemplary embodiments of the present invention will be described in greater detail below with reference to the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
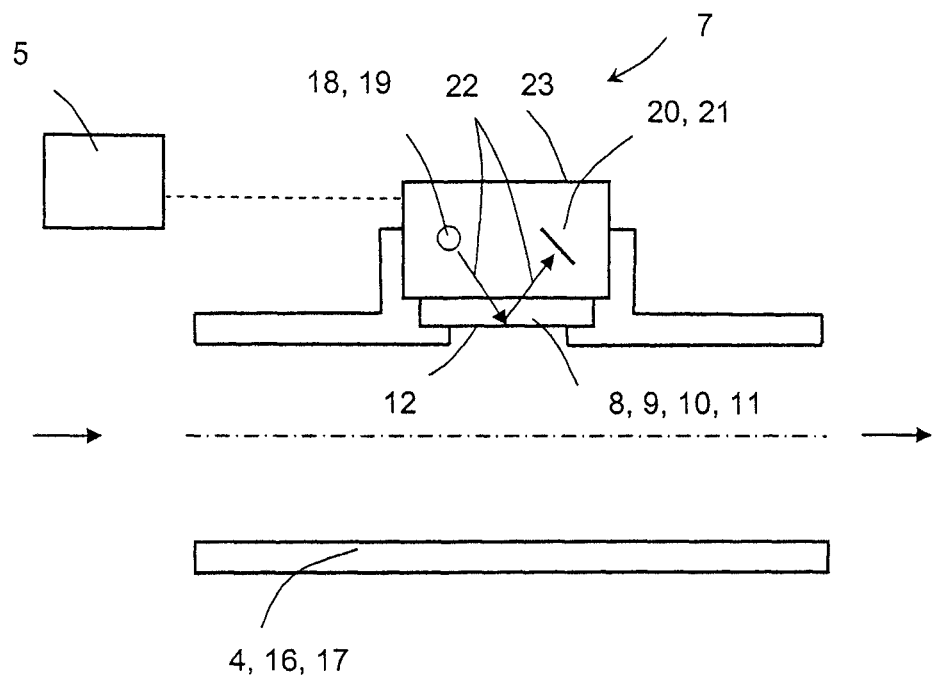
FIG. 1 is a schematic section of a dew sensor arranged in a gas channel.

Referring to the drawings in particular, FIG. 1 shows a section of an optical dew sensor 7, which is arranged at a gas channel 4 designed as an inspiration or expiration tube 16, 17. A sample holder and/or a wall 11 made of glass 10, i.e., a solid 9, is formed at the gas channel 4. A generating means for electromagnetic radiation 18, designed as a transmitting diode 19, generates a light beam 22, which is sent to and through the wall 11. The light beam 22 is reflected at a boundary surface 12 between the wall 11 as the medium 8 with a higher optical density and the breathing air flowing in the gas channel 4 as the medium with the lower optical density and subsequently detected by a detection means for electromagnetic radiation 20, which is designed as a receiving diode 21.

The light beam 22 is reflected at the boundary surface 12 according to the law of reflection with an angle of incidence equal to the reflection angle. The angle of incidence is preferably selected to be such that the light beam 22 is totally reflected and the angle of incidence thus corresponds to the critical angle of the total reflection. According to the Snellius law of refraction, the light beam 22 can also be refracted at the boundary surface 12, and the refracted light beam 22 (not shown) is not detected by the receiving diode 21.

Humidity is contained in the breathing air being sent through the gas channel 4. The humidity present in the air condenses at high relative humidity of the air in the breathing air, especially in the range of 100%, and precipitates on the wall 11 and hence at the optical boundary surface 12 in the form of water drops or a water film. The condensed water present at the boundary surface 12 changes the refractive index, so that the light beam 22 is no longer reflected totally at the boundary surface 12 but is partially refracted as well. Thus, only the partially reflected light beam 22 is detected by the receiving diode 21. The optical change in the reflection of the light beam 22 is thus detected by the receiving diode 21 and transmitted to a control and/or regulating unit 5. The change in the reflection of the light beam at the boundary surface 12 is an indicator of a change in dew formation at this boundary surface 12 and hence of the humidity in the breathing air in the gas channel 4. The control and/or regulating unit 5 analyzes the data of the receiving diode 21 and thus determines the humidity in the breathing air or a limit value of the humidity in the breathing air. The dew sensor 7 is thus an optical dew sensor. The transmitting and receiving diodes 19, 21 are arranged in a sensor housing 23. The sensor housing 23 can be easily attached to and removed from the gas channel 4 when the inspiration or expiration tube 16, 17 is replaced. Only the wall 11 remains as a window in the tube 16, 17 in order to prevent cross contamination between different patients.

Figure 2:
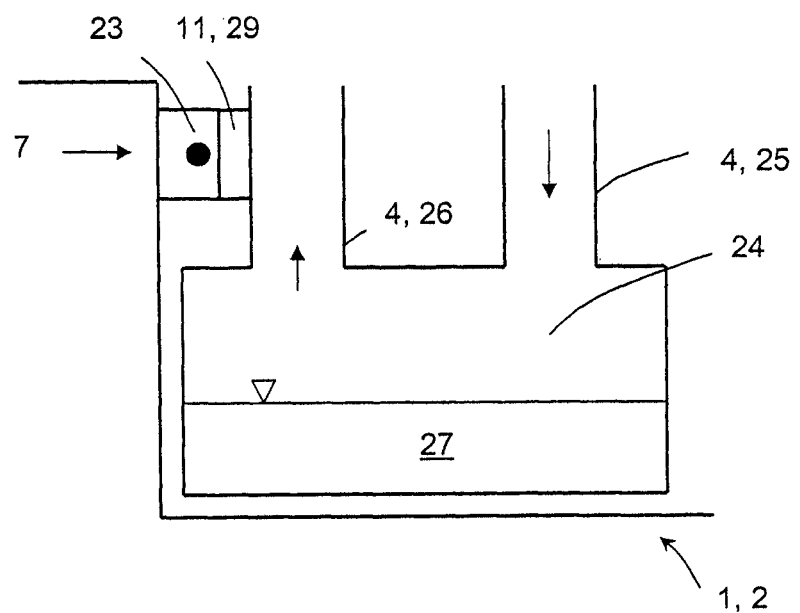
FIG. 2 is a schematic section of a humidifying chamber of a respiration humidifier with a dew sensor arranged at an outlet pipe.
Figure 3:
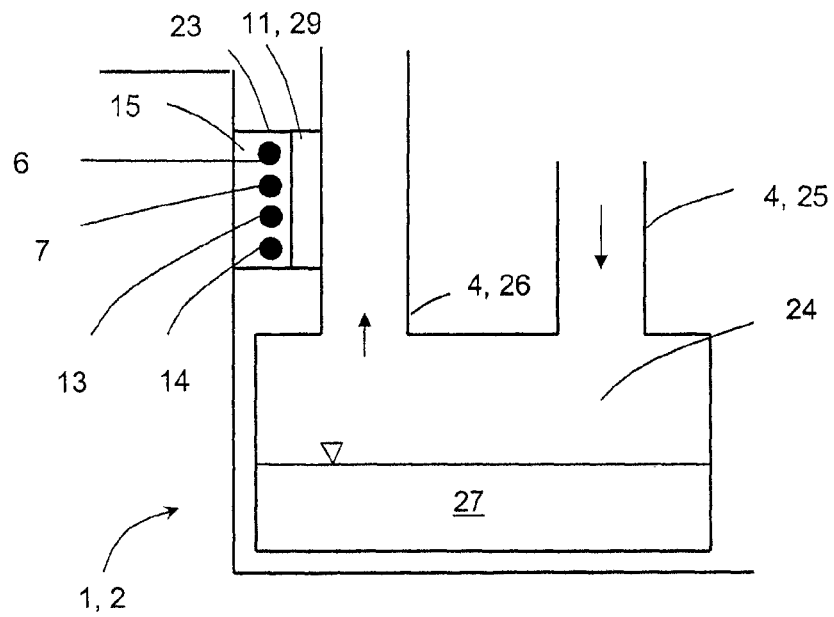
FIG. 3 is a schematic section of the humidifying chamber of the respiration humidifier with a sensor block with the dew sensor arranged at the outlet pipe.

FIGS. 2 and 3 show two different possibilities of arrangement of the dew sensor 7 at the humidifying chamber 24 with water 27 of a respiration humidifier 2. An inlet pipe 25 and an outlet pipe 26 are formed at the humidifying chamber 24. The outlet pipe 26 is manufactured with a wall 11, in which a window 29 is formed for coupling with the dew sensor 7. The sensor housing 23 with the transmitting and receiving diodes 19, 21 is detachably fastened to the wall 11 (FIG. 2). In addition, a sensor 13 for the concentration of $CO_2$ and a sensor 14 for the breathing gas volume flowing in as well as a temperature sensor 6 can be integrated in the sensor housing 23, so that a sensor block 15 is present (FIG. 3). Furthermore, the dew sensor 7 may also be installed analogously in the inspiration or expiration tube 16, 17 (FIG. 4).

Figure 4:
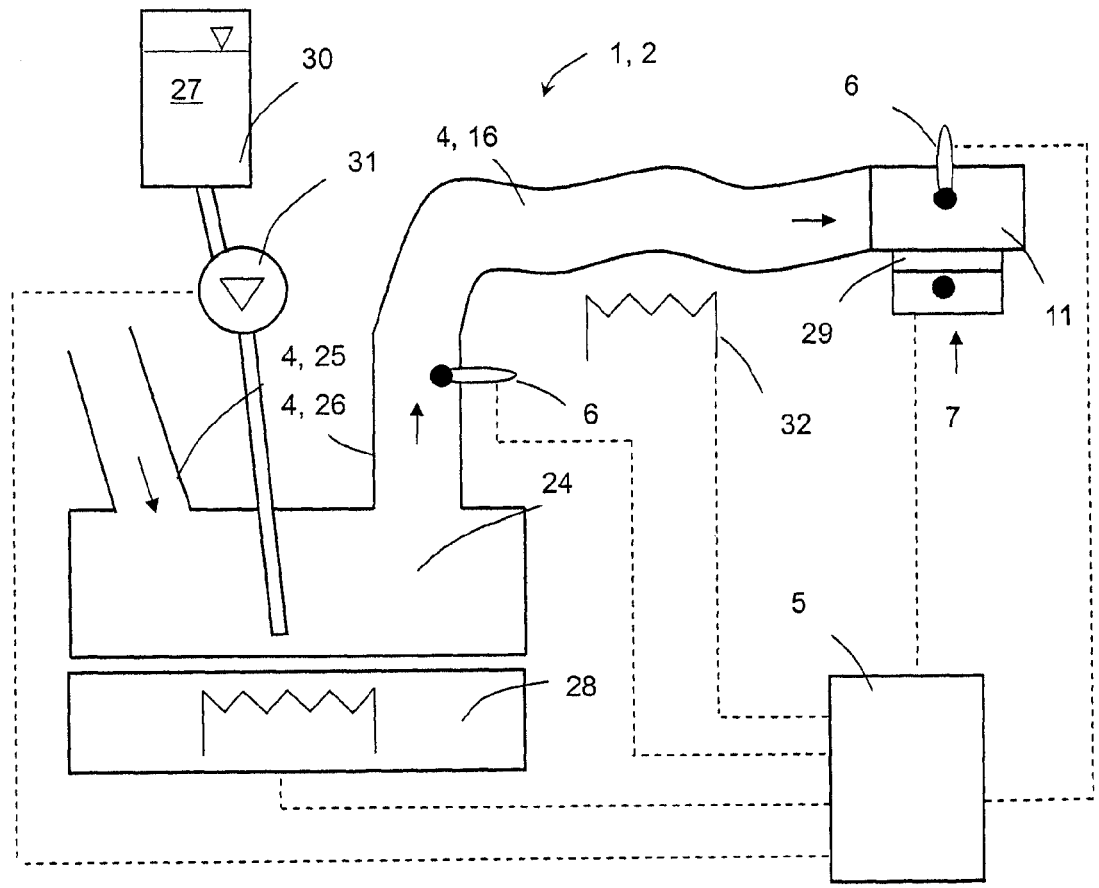
FIG. 4 is a schematic section of the respiration humidifier with a dew sensor arranged at an inspiration tube and with a liquid dispensing unit.

FIG. 4 shows a schematic section of the respiration humidifier 2 with a dew sensor 7 arranged at the inspiration tube 16 and with a liquid dispensing unit 31. The liquid dispensing unit 31 is controlled and/or regulated by a control and regulating unit 5, which dispenses a defined quantity of liquid necessary for humidifying the breathing air. The breathing air to be humidified flows for this through an inlet pipe 25 into the humidifying chamber 24 and leaves same through an outlet pipe 26. A sensor 14 for measuring the breathing gas volume flow (breathing gas volume per unit of time) (not shown) may be optionally provided at the inlet pipe 25. Water 27 can be fed into the humidifying chamber 24 from a container 30 by means of the liquid dispensing unit 31, and the water 27 evaporates from a heater 28 arranged in the humidifying chamber 24. The temperature of the heater 28 is adjusted to a constant value. A temperature sensor 6 each is arranged at the outlet pipe 26 and at the end of the inspiration tube 16. Furthermore, the dew sensor 7 is positioned at the end of the inspiration tube 16. The two temperature sensors 6, the dew sensor 7, heater 28 for the water 27, the tube heater 32 and the dispensing unit 31 are connected to a control and regulating unit 5, so that the data detected by the sensors 6 and 7 can be transmitted for analysis to the control and regulating unit 5. The dispensing unit 31, the heater 28 and the tube heater 32 can be controlled and/or regulated by the control and regulating unit 5, corresponding to the values determined for dew formation at the boundary surface 12 of the dew sensor 7, the water 27 is dispensed by the liquid dispensing unit 31. The humidity of the breathing gas is thus regulated by regulating the quantity of water 27 that is fed to the heater 28 via the liquid dispensing unit 31.

Figure 5:
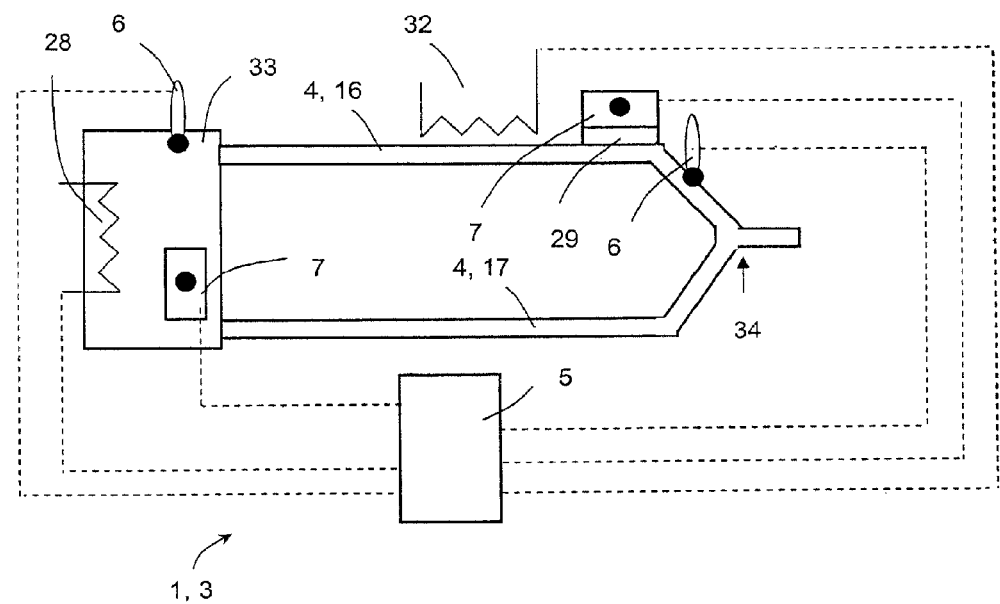
FIG. 5 is a schematic section of an anesthesia reflector with a dew sensor arranged at the inspiration tube.

FIG. 5 shows an anesthesia reflector 3. The inspiration gas as the breathing air to be breathed in is sent through the inspiration tube 16 and through a Y-piece 34 to a patient. The breathing air breathed out by the patient is sent as expiration gas through the expiration tube 17 to a reflector unit 33 for anesthetic. The anesthetic is reflected onto the inspiration gas in the reflector unit 33 and the inspiration gas is humidified. The inspiration gas is sent through the reflector unit 33 before it flows through the inspiration tube 16. A temperature sensor 6 each and a dew sensor 7 each are arranged in the reflector unit 33 and at the end of the inspiration tube 16 in the area of the Y-piece 34. The inspiration tube 16 can be heated by means of a tube heater 32. A heater 28 for the reflector unit 33 makes it possible to heat the reflector unit 33 as well.

The two temperature and dew sensors 6, 7, heater 28 for the reflector unit 33 and the tube heater 32 are connected to a control and regulating device 5 for analysis. The heater 28 and the tube heater 32 can be controlled and/or regulated by the control and regulating unit 5. Condensation is to be avoided in the anesthesia reflector 2 in the inspiration tube 16 and in the reflector unit 33.

When the anesthesia reflector 3 is switched on, the inspiration gas is at first heated with heater 28 until the temperature sensor 6 arranged in the reflector unit 33 detects a preset temperature. At the same time, the actual value of the inspiration temperature is detected at the end of the inspiration tube 16 by the temperature sensor 6 arranged there and the set point of the inspiration temperature is controlled and/or regulated by means of the tube heater 32. As soon as dew formation is detected at one of the two dew sensors 7, the set point of the preset temperature of the breathing air is reduced at the temperature sensor 6 of the reflector unit 33 by the heating output of the tube heater 32 being reduced. This is carried out until dew formation declines or no dew formation occurs any longer. If no dew formation is detected any longer, the preset temperature of the breathing air is slightly raised at the temperature sensor 6 of the reflector unit 33. This operation is carried out in a control loop, so that the heating output of heater 28 and/or of the tube heater 32 is regulated around the dew point at the two dew sensors 7. The heating output of the heater 28 and/or of the tube heater 32 is thus controlled and/or regulated by means of the control and/or regulating unit 5 such that dew formation is avoided or maintained at a low level in the inspiration tube 16 as well as preferably also in the expiration tube 17 and in the reflector unit 33.

Figure 6:
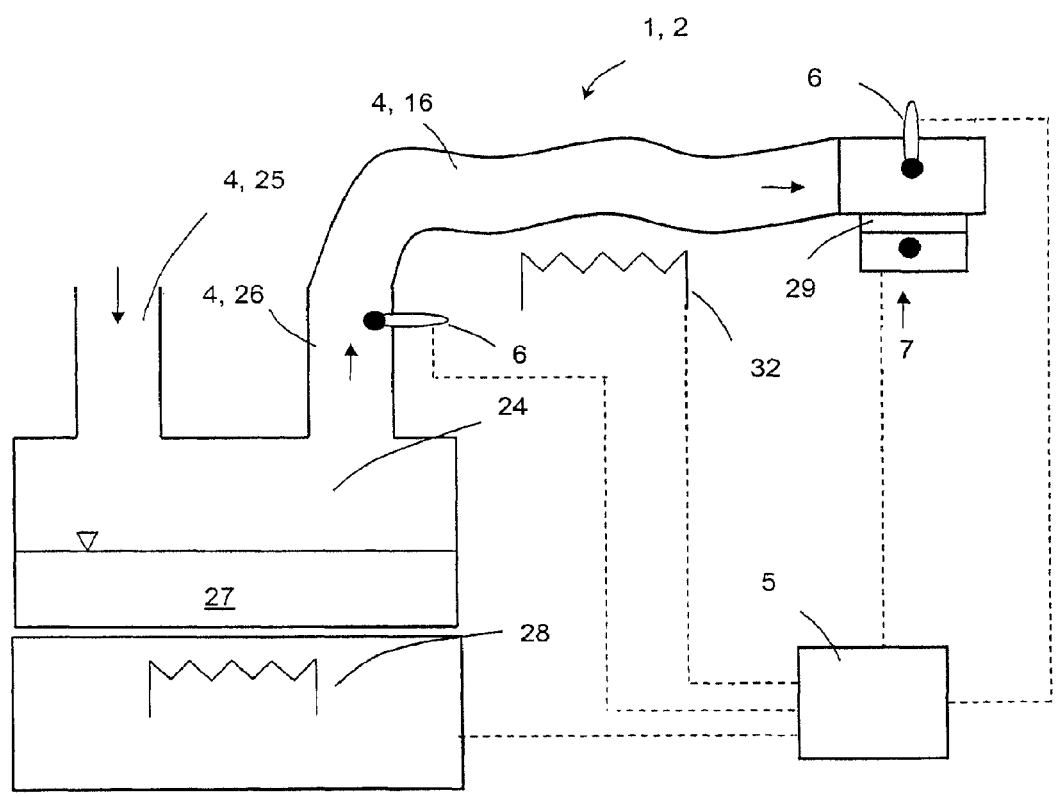
FIG. 6 is a schematic section of the respiration humidifier with a dew sensor arranged at an inspiration tube.

FIG. 6 shows a respiration humidifier 2 with the humidifying chamber 24 and with a heater 28 for the humidifying chamber 24. The breathing air to be humidified flows through an inlet pipe 25 into the humidifying chamber 24 containing water 27 and leaves same through an outlet pipe 26. The water can be heated with the heater 28 and the relative and absolute humidity in the inspiration gas flowing through the outlet pipe 26, which inspiration gas is sent to the patient through an inspiration tube, can thus be controlled and/or regulated. A temperature sensor 6 each is arranged at the outlet pipe 26 and at the end of the inspiration tube 16. Furthermore, the dew sensor 7 is positioned at the end of the inspiration tube 16. The inspiration tube 16 can be heated by a tube heater 32. The two temperature sensors 6, dew sensor 7, heater 28 for the water 27 and the tube heater 32 are connected to a control and regulating unit 5, so that the data detected by the sensors 6, 7 can be transmitted to the control and regulating unit 5 for analysis. The heater 28 and the tube heater 32 can be controlled and/or regulated by the control and regulating unit 5. The heater 28 and hence the evaporation of the water 27 are regulated corresponding to the values determined for the dew formation at the boundary surface 12 of the dew sensor 7. The heating output of the heater 28 and/or of the tube heater 32 is thus controlled and/or regulated by means of the control and/or regulating unit 5 such that dew formation is avoided or maintained at a low level in the inspiration tube 16 as well as preferably also in the expiration tube 17 and in the reflector unit 33.

On the whole, considerable advantages are associated with the device 1 for respirating patients. The dew sensor 7 can measure dew formation with certainty and reliably and it can be manufactured at a low cost. Cross infection is not possible, because the wall 11 remains at the tubes 16, 17 when a tube 16, 17 is replaced and the sensor housing 23 with the transmitting and receiving diodes 19, 21 can be easily attached to another tube 16, 17 with a corresponding wall 11.

The optical measurement method has the advantage that no cables need to be used inside the tube 16, 17. Furthermore, condensation can be avoided in the respiration system.

While specific embodiments of the invention have been shown and described in detail to illustrate the application of the principles of the invention, it will be understood that the invention may be embodied otherwise without departing from such principles.

APPENDIX

List of Reference Numbers

1 Device for respirating patients
2 Respiration humidifier
3 Anesthesia reflector
4 Gas channel
5 Control and/or regulating unit
6 Temperature sensor
7 Dew sensor
8 Medium with the higher optical density
9 Solid
10 Glass
11 Wall
12 Boundary surface
13 Sensor for $CO_2$ measurement
15 Sensor block
16 Inspiration tube
17 Expiration tube
18 Generating means for electromagnetic radiation
19 Transmitting diode
20 Detection means for electromagnetic radiation
21 Receiving diode
22 Light beam
23 Sensor housing of the dew sensor
24 Humidifying chamber
25 Inlet pipe
26 Outlet pipe
27 Water
28 Heater
29 Window
30 Tank
31 Liquid dispensing unit
32 Tube heater
33 Reflector unit for anesthetic
Y-piece

What is claimed is:

1. A device for respirating patients, respiration humidification or for an anesthesia reflector, the device comprising:
   humidification/anesthetic concentration means for increasing the humidity and/or the anesthetic concentration in breathing gas;
   a gas channel for passing through breathing gas;
   a medium having an optical density higher than that of breathing gas and defining a boundary surface between the breathing gas and said medium;
   a control and/or regulating means connected to the humidification/anesthetic concentration means;
   a temperature sensor connected to the control and/or regulating means; and
   a dew sensor for measuring the humidity contained in the breathing air, said dew sensor including a generating means for generating electromagnetic radiation and said medium allowing at least a portion of the generated electromagnetic radiation to pass through the medium and said dew sensor including a detection means for detecting electromagnetic radiation, wherein said dew sensor determines a change in a reflection of electromagnetic radiation at the boundary surface between the breathing gas and the medium having the optical density higher than that of breathing gas as an indicator of a change in dew formation at said boundary surface, said control and/or regulating means being connected to said dew sensor and acting on the humidification/anesthetic concentration means for increasing the humidity in the breathing gas until the humidity reaches a limit value corresponding to the detected change in dew formation at said boundary surface.

2. A device for respirating patients in accordance with claim 1, wherein the medium having the higher optical density is a solid.

3. A device for respirating patients in accordance with claim 1, wherein the medium having the higher optical density is glass or a plastic transparent to electromagnetic radiation.

4. A device for respirating patients in accordance with claim 2, wherein the medium having the higher optical density comprises a methyl methacrylate.

5. A device for respirating patients in accordance with claim 1, wherein the boundary surface is arranged at the humidification/anesthetic concentration means for increasing the humidity and/or the anesthetic concentration in the breathing gas.

6. A device for respirating patients in accordance with claim 2, further comprising a heater, wherein the solid is heated by said heater.

7. A device for respirating patients in accordance with claim 1, further comprising additional sensors for sensing parameters including one or more of temperature, $CO_2$ or breathing gas volume, said additional sensors being integrated into a sensor block arranged at said dew sensor.

8. A device for respirating patients in accordance with claim 2, wherein said solid of said medium having the higher optical density comprises one of a sample holder and a wall of said gas channel and a housing of said humidification/anesthetic concentration means for increasing the humidity and/or the anesthetic concentration in the breathing gas.

9. A process for controlling and/or regulating the humidity of breathing gas in a device for respirating patients, the process comprising the steps of:
   providing a humidification/anesthetic concentration means for increasing the humidity and/or the anesthetic concentration in breathing gas;
   providing a gas channel for passing through breathing gas;
   providing a control and/or regulating means;
   providing a medium having an optical density higher than that of breathing gas, the medium having a surface defining a boundary surface between the breathing gas and said medium;
   providing a temperature sensor;
   providing a dew sensor including a generating means for generating electromagnetic radiation and introducing the generated electromagnetic radiation into the medium and a detection means for detecting electromagnetic radiation, wherein said dew sensor determines a change in a reflection of electromagnetic radiation at a boundary surface between the breathing gas and the medium having the optical density higher than that of breathing gas as an indicator of a change in dew formation at said boundary surface;
   measuring the humidity contained in the breathing gas by means of the dew sensor;
   analyzing data determined by the dew sensor and controlling and/or regulating the humidity of the breathing gas on the basis of the data measured by the dew sensor, wherein the detection of the humidity of the breathing gas comprises the following steps:

generating an electromagnetic radiation;
sending the electromagnetic radiation to the boundary surface between breathing gas and the medium having the optical density higher than that of breathing gas with at least partial reflection of the electromagnetic radiation at the boundary surface;

detecting the electromagnetic radiation reflected at the boundary surface only, analyzing the quantity of reflected electromagnetic radiation to determine the change in dew formation at the boundary surface; and increasing the humidity in the breathing gas until, with the humidification/anesthetic concentration means such that the humidity reaches a limit value corresponding to a detected change in dew formation at said boundary surface.

10. A process in accordance with claim 9, wherein the humidity in the breathing gas is increased until a reduction in the reflection of the electromagnetic radiation appears because of the formation of water of condensation on the surface of the medium having the higher optical density.

11. A process in accordance with claim 10, wherein the medium having the higher optical density is heated during the formation of water of condensation on the surface of the medium having the higher optical density in order to evaporate the water of condensation.

12. A process in accordance with claim 9, wherein the humidity in the breathing gas is reduced when a limit value of the humidity in the breathing gas is reached.

13. A process in accordance with claim 9, wherein the humidity in the breathing gas is reduced when the reflection of the electromagnetic radiation decreases because of the formation of water of condensation on the surface of the medium having the higher optical density.

14. A process in accordance with claim 9, wherein controlling and/or regulating the humidity of the breathing gas on the basis of the data measured by the dew sensor includes raising or lowering the temperature in the humidifying chamber of a respiration humidifier to increase or reduce of the humidity in the breathing gas.

15. A respiration device comprising:
a breathing gas channel carrying breathing gas;
humidification/anesthetic concentration means for increasing the humidity and/or the anesthetic concentration in the breathing gas;
a control and/or regulating means for regulating said humidification/anesthetic concentration means, said control and/or regulating means being connected to said humidification/anesthetic concentration means;

a temperature sensor connected to said control and/or regulating means; and a dew sensor for measuring the humidity contained in the breathing gas, said dew sensor being connected to said control and/or regulating means and comprising:

an electromagnetic radiation generating means for generating electromagnetic radiation;
an electromagnetic radiation detection means for detecting electromagnetic radiation;
a medium having an optical density higher than that of the breathing gas and allowing at least a portion of the generated electromagnetic radiation to pass through the medium, said medium having a first side and having an opposite second side defining a boundary surface positioned in contact with the breathing gas, said electromagnetic radiation generating means directing generated electromagnetic radiation at said boundary surface by introducing the generated electromagnetic radiation at said first side such that is passes through said medium to said boundry surface and said electromagnetic radiation detection means receiving electromagnetic radiation reflected at said boundary surface after passing through said medium from said second side to said first side, to determine a change in a reflection of electromagnetic radiation at said boundary surface, said control and/or regulating means acting on the humidification/anesthetic concentration means for increasing the humidity in the breathing gas until a reduction in the reflection of the electromagnetic radiation occurs because of the formation of water of condensation on the surface of the medium.

16. A device in accordance with claim 15, wherein the medium having the higher optical density is a solid glass or a plastic transparent to the generated electromagnetic radiation, the solid glass or plastic forming or defining at least a part of said breathing gas channel.

17. A device in accordance with claim 16, wherein the boundary surface is arranged at the humidification/anesthetic concentration means for increasing the humidity and/or the anesthetic concentration in the breathing gas.

18. A device in accordance with claim 16, further comprising a heater for heating the solid.

19. A device in accordance with claim 15, further comprising additional sensors for sensing parameters including one or more of temperature, $CO_2$ or breathing gas volume, said additional sensors being integrated into a sensor block arranged at said dew sensor.

* * * * *